United States Patent
Harbers et al.

(10) Patent No.: US 9,322,765 B2
(45) Date of Patent: Apr. 26, 2016

(54) LIGHT SOURCE LIFETIME EXTENSION IN AN OPTICAL SYSTEM

(71) Applicant: Roche Diagnostics Operations, Inc., Indianapolis, IN (US)

(72) Inventors: Rik Harbers, Cham (CH); Philipp Nicolas Zeller, Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 202 days.

(21) Appl. No.: 14/303,644

(22) Filed: Jun. 13, 2014

(65) Prior Publication Data

US 2014/0291557 A1 Oct. 2, 2014

Related U.S. Application Data

(63) Continuation of application No. PCT/EP2012/075228, filed on Dec. 12, 2012.

(30) Foreign Application Priority Data

Dec. 22, 2011 (EP) .................................... 11195351

(51) Int. Cl.
*G01N 21/01* (2006.01)
*G01J 1/08* (2006.01)
(Continued)

(52) U.S. Cl.
CPC . *G01N 21/01* (2013.01); *G01J 1/08* (2013.01); *G01J 3/0286* (2013.01); *G01J 3/10* (2013.01); *G01N 21/17* (2013.01); *H05B 33/0821* (2013.01)

(58) Field of Classification Search
CPC ... G01N 21/01; G01N 21/17; H05B 33/0281; G01J 1/08; G01J 3/10; G01J 3/0286

USPC ................................ 250/578.1; 315/362, 112
See application file for complete search history.

(56) References Cited

U.S. PATENT DOCUMENTS

2005/0279949 A1 12/2005 Oldham et al.
2006/0121602 A1 6/2006 Hoshizaki et al.
(Continued)

FOREIGN PATENT DOCUMENTS

CN 201311392 Y 9/2009
EP 1962084 A1 8/2008
(Continued)

OTHER PUBLICATIONS

International Search Report issued Feb. 8, 2013, in Application No. PCT/EP2012/075228, 7 pages.
(Continued)

*Primary Examiner* — Seung C Sohn
(74) *Attorney, Agent, or Firm* — Roche Diagnostics Operations, Inc.

(57) ABSTRACT

An optical system comprising a light source comprising a plurality of light emitting elements (LEEs) is presented. The light source is mounted on the same substrate or chip board so that the LEEs are in thermal contact with each other such as to enable thermic conduction and heat transfer between the LEEs. The system is switchable between light source modes in which different light emitting elements or a different number of light emitting elements is switched in an on mode and in a down mode respectively. In all light source modes, one or more light emitting elements, such as those with longer expected lifetime, remain in the on mode, while one or more light emitting elements, such as those with shorter expected lifetime, may be switched in the down mode.

15 Claims, 3 Drawing Sheets

(51) Int. Cl.
*G01J 3/10* (2006.01)
*G01J 3/02* (2006.01)
*G01N 21/17* (2006.01)
*H05B 33/08* (2006.01)

(56) References Cited

U.S. PATENT DOCUMENTS

2006/0202133 A1* 9/2006 Ok .................. G01J 3/02
250/458.1
2008/0280331 A1* 11/2008 Davies .............. B01L 7/525
435/91.2

FOREIGN PATENT DOCUMENTS

| | | |
|---|---|---|
| JP | 2008-249411 A | 10/2008 |
| WO | 2002/059592 A2 | 8/2002 |
| WO | 2007/021461 A1 | 2/2007 |

OTHER PUBLICATIONS

Malinen, Jouko et al., "LED-based NIR spectrometer module for hand-held and process analyzer applications," Sensors and Actuators B Chemical, 1998, pp. 220-226, vol. B 51.

* cited by examiner

LIGHT SOURCE LIFETIME EXTENSION IN AN OPTICAL SYSTEM

CROSS-REFERENCE TO RELATED APPLICATIONS

This application is a continuation of PCT/EP2012/075228 filed Dec. 12, 2012, which is based on and claims priority to EP 11195351.9 filed Dec. 22, 2011, which is hereby incorporated by reference.

BACKGROUND

The present disclosure generally relates to optical systems and methods for photometric measurement of samples and, in particular, to optical systems for photometric measurement of samples that comprise a light source comprising a plurality of light emitting elements and to a method of controlling the light source.

Various types of tests related to patient diagnosis and therapy can be performed by analysis of a patient's liquid sample. Such samples are typically placed in sample tubes. For analysis, they are extracted from the tubes, combined with various reagents, incubated, and analyzed. In typical clinical chemical and immunochemical analyses, one or more assay reagents are added to a liquid sample; the sample-reagent combination is mixed and incubated within an optical cuvette. In the course of the reaction, a change in optical properties occurs such as, for example, a variation of absorption, scattering or fluorescence of the sample. Normally an optical system is used to carry out a photometric measurement before, during and/or after the reaction, for example, by measuring the optical transmission through the cuvette using a beam of light generated by a light source and illuminating the sample-reagent combinations in such optical cuvettes. The results are used to generate extinction data, which are the ratio between light intensity input and output after passing the sample. In this way, the presence and/or concentration of analytes in a sample, which may be indicative of a diagnostic condition, can be determined by measuring response signals by a detector, typically at particular wavelengths. Examples of such photometric measurements comprise turbidimetric, fluorometric and absorption measurements and the like.

Different types of light sources may be used. These may comprise one or more light emitting elements. Examples of typically used light emitting elements are electric powered radiation sources such as incandescent lamps, electroluminescent lamps, gas discharge lamps, high-intensity discharge lamps, light emitting diodes (LEDs). Different types of light emitting elements but also light emitting elements of the same type, such as different LEDs, may emit light of different wavelengths. In particular, there are light emitting elements emitting light with a broad wavelength spectrum or with different respective wavelengths or wavelength bands.

It is known that temperature variations in a light source may cause changes in the emission intensity as well as shifts in the spectral emission. For example, the operational temperature of an LED, more specifically its junction temperature, has a direct influence on the wavelength of its light, the light intensity and the power resulting from the applied current. The junction temperature rises by heating due to dissipation of the electrical power, and is also affected by the ambient temperature. On the other hand, in order to perform a reliable and reproducible optical analysis it is important to maintain the emission intensity constant and to prevent spectral shifts.

For this reason, control of the temperature of the light source is normally necessary. As the junction temperature usually cannot be directly measured, the socket temperature can be used for temperature control of an LED, as it is closely related to the junction temperature.

Generally, the lifetime of a light source depends also on the temperature of the light emitting elements under operational conditions, i.e. when emitting light. Extending the lifetime of a light source is important because replacing the light source may be an expensive process, involving administrative overhead as well as labor. Moreover, it causes system downtime, during which time the system cannot be used. The total cost can thus be several times higher than the purchase cost of the light source itself. The life time of a light source comprising LEDs, for example, depends on the junction temperature under operational conditions. Lower junction temperatures and smaller temperature variations (less thermal stress) increase the lifetime of the whole LED. Moreover, different light emitting elements may have different lifetimes, i.e. a varying resistance to the operational conditions. This is also the case for different LEDs. In particular, LEDs emitting light of different wavelengths may have different lifetimes.

Controlling the temperature of a light source, especially cooling the light source, is therefore important also for extending the lifetime of light emitting elements.

Another possible way of extending the lifetime of a light source would be that of switching the light source off when not needed. However, switching the light source off and on again would cause temperature instabilities because of the time needed to reach a stable and reproducible operational temperature every time. Temperature instabilities cause in turn changes in emission intensities and spectral instabilities as described above. In order to prevent temperature instabilities, one possibility is to quickly pulse between on and off, for example, within microseconds. However, pulsing during a measurement leads to a loss of emission intensity, meaning less light available for the measurement during the measurement time, which is a drawback. Another possibility is to pre-heat the light source before switching the light source on again. This however requires temperature measurement and accurate temperature control, which may be complicated and difficult to obtain, especially in high-throughput systems.

Therefore, this is a need for an optical system and a method that can extend the lifetime of the light source while increasing temperature stability.

SUMMARY

According to the present disclosure, an optical system and a method for the photometric measurement of samples is presented. The optic system can comprise a light source. The light source can comprise a plurality of light emitting elements (LEEs) mounted on the same substrate or chip board in thermal contact with each other such as to enable thermic conduction and heat transfer between the LEEs. The LEEs can have different expected lifetimes. The optical system can further comprise a controlling unit for switching the optical system between at least two light-source modes chosen from at least one light-source-lifetime-extending mode (LEM) and at least one light-source-lifetime-non-extending mode (non-LEM). In the at least one LEM, at least one light emitting element with shorter expected lifetime (S-LEE) can be in a down mode. In the at least one non-LEM, all S-LEEs can be in an on mode. In the at least one LEM and in the at least one non-LEM, at least one light emitting element with longer expected lifetime (L-LEE) can be in the on mode.

In accordance with one embodiment of the present disclosure, a temperature regulator to maintain the light source within a light-source mode temperature range is also part of the optical system. In different LEMs respectively, different LEEs, or a different number of LEEs are in the down mode. At least one LEE is in the on mode.

Accordingly, it is a feature of the embodiments of the present disclosure to provide an optical system and a method that can extend the lifetime of the light source while increasing temperature stability. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An optical system for the photometric measurement of samples is presented. The system can comprise a light source comprising a plurality of light emitting elements (LEEs) mounted on the same substrate or chip board in thermal contact with each other such as to enable thermic conduction and heat transfer between the LEEs. According to one embodiment, the LEEs can have different expected lifetimes. This can mean that there is at least one light emitting element with shorter expected lifetime (S-LEE) and at least one light emitting element with longer expected lifetime (L-LEE). The system can comprise a controlling unit for switching the system between at least two light-source modes chosen from at least one light-source-lifetime-extending mode (LEM) and at least one light-source-lifetime-non-extending mode (non-LEM). In one embodiment, in the at least one LEM, at least one S-LEE can be in a down mode, in the at least one non-LEM, all the S-LEEs can be in an on mode, and in all light-source modes at least one L-LEE can be in the on mode.

An "optical system" can be either a self-standing instrument, or an integrated component, within an analyzer or a module within an analytical system, suitable for the optical analysis of analytes present in a sample and particularly for measuring the optical transmission through a sample or emission light from an illuminated sample.

The optical system can particularly be suitable for analyzing biological samples. Samples can be, for example, liquid solutions in which one or more analytes of interest can be potentially found, such as body fluids like blood, serum, plasma, urine, milk, saliva, cerebrospinal fluid, and the like. Samples may be analyzed as such or after being diluted with another solution or after having being mixed with reagents, for example, to carry out one or more diagnostic assays like, for example, clinical chemistry assays, immunoassays, molecular diagnostic assays such as nucleic acid tests. Thus the optical system may advantageously be used to detect the result of a chemical or biological reaction or to monitor the progress of a chemical or biological reaction, for example, in a coagulation assay, agglutination assay, turbidimetric assay, nucleic acid assay and the like.

A "light source" can be a unit within the optical system comprising a plurality of, i.e. at least two, light emitting elements capable of emitting light, typically of selected wavelength or wavelengths or wavelength bands.

A "light emitting element" can be an electrically powered radiation source such as an incandescent lamp, an electroluminescent lamp, a gas discharge lamp, a high-intensity discharge lamp, a laser and the like.

According to one embodiment, the light emitting elements can be light emitting diodes.

The term "light emitting diode" or "LED" can be used herein to refer to conventional light-emitting diodes, i.e., inorganic semiconductor diodes that can convert applied electrical energy to light. Such conventional LEDs include, for example, aluminum gallium arsenide (AlGaAs), which generally produce red and infrared light, gallium aluminum phosphide, which generally produce green light, gallium arsenide/phosphide (GaAsP), which generally produce red, orange-red, orange, and yellow light, gallium nitride, which generally produce green, pure green (or emerald green), and blue light, gallium phosphide (GaP), which generally produce red, yellow and green light, zinc selenide (ZnSe), which generally produce blue light, indium gallium nitride (InGaN), which generally produce bluish-green and blue light, indium gallium aluminum phosphide, which generally produce orange-red, orange, yellow, and green light, silicon carbide (SiC), which generally produce blue light, diamond, which generally produce ultraviolet light, and silicon (Si), which are under development. LEDs may not be limited to narrowband or monochromatic light LEDs. LEDs may also include broad band, multiple band, and generally white light LEDs.

The term LED can also be used herein to refer to Organic Light Emitting Diode (OLED), that can be polymer-based or small-molecule-based (organic or inorganic), edge emitting diodes (ELED), Thin Film Electroluminescent Devices (TFELD), Quantum dot based inorganic "organic LEDs," and phosphorescent OLED (PHOLED).

Thus, according to certain embodiments, the LED can be a standard semiconductor device, an organic LED, or an inorganic LED. Examples of organic LEDs are QDOT-based LEDs and a nanotube-based LEDs. The LED can be a stack of LED's such as a stack of organic LEDs or a stack of organic LED layers.

According to one embodiment, the light source can comprise a plurality, i.e. a number equal to or greater than 2, of LEDs with different respective wavelengths or wavelength bands. For example, the light source may comprise a combination of two, three, or more LEDs, such as, having a first relatively short wavelength spectrum (e.g. UV-blue) LED, a second longer wavelength spectrum LED, a third even longer wavelength spectrum LED and so on up to eventually the infrared wavelengths depending on the wavelengths needed. A white LED or an LED capable of emitting light with a broad spectrum may also be present. Of course, the light source may comprise more than one LED for each wavelength or wavelength band. Also, different wavelength bands may be at least in part overlapping.

According to one embodiment, the LEEs can have "different expected lifetimes". This can mean that, when comparing between them LEEs of the same light source, one can have a shorter expected lifetime and one can have a longer expected lifetime respectively. In relative terms, longer expected lifetime can mean at least twice longer than the expected lifetime of the LEE with the shortest expected lifetime. "Lifetime", in general, can be intended as lifetime under operational conditions, i.e. the expected number of hours that a light emitting element can emit light or light of a certain emission intensity from the same light source. In general, L-LEEs can be expected to last longer or can emit light for a larger number of hours than times-LEEs. It is to be understood that the "lifetime of an LEE" can refer to an expected lifetime and that the actual lifetime of an LEE may be different from the expected lifetime. As an example, identical LEEs can have the same expected lifetime, but it can be unlikely that they can last for exactly the same time, even under the same operational conditions. Thus, even if they are identical, they might have different actual lifetimes. In general, however, the higher the expected lifetime is, the higher can be the average actual lifetime. The expected lifetime can be either calculated according to the physical chemical characteristics of the LEE and/or from an average of measured actual lifetimes, e.g. in terms of the time by which a certain percentage of the population of a given type of LEEs can be expected to have failed. The "average expected lifetime" can be the time when 50% of a given population of the same type of LEEs can be expected to have failed.

Usually, incandescent LEEs can display little change in emission intensity until the bulb fails nearly suddenly. LEEs such as LEDs, on the other hand, do not tend to fail suddenly. Instead, the emission intensity can degrade gradually over time. Typical lifetimes, i.e. expected lifetimes, can be quoted between about 25,000 and about 100,000 hours but heat and current settings can extend or shorten this time significantly. The most common symptom of LEDs failure as well as diode lasers failure can be the gradual lowering of emission intensity and loss of efficiency. Sudden failures, although rare, can occur as well. As already mentioned, in order to perform a reliable and reproducible optical analysis, it can be important to maintain the emission intensity constant and prevent spectral shifts. When the light level falls below a specified minimum, replacement of a light emitting element or of the entire light source may be required. In other words, the light source can be said to have failed when the light level of at least one light emitting element falls below a specified threshold under operational conditions. This threshold may be set as high as, for example, about 90% or higher compared to the original emission intensity.

The "light-source expected lifetime" can therefore be defined as the lifetime of the LEE with the shortest expected lifetime, i.e. the expected lifetime or the time until its emission intensity is expected to fall below an acceptable minimum. The actual lifetime can depend however on the actual lifetime of the LEE with the shortest actual lifetime, which might be an S-LEE other than that with the shortest expected lifetime. Extending the light-source lifetime thus can mean increasing the expected lifetime of one or more S-LEEs.

According to one embodiment, the system can be switchable between at least two light-source modes chosen from at least one LEM and at least one non-LEM. This can mean switchable between a LEM and a non-LEM and/or vice versa and/or switchable between a LEM and at least another LEM. A "light-source mode" can be one of a plurality of possible modes, at least two, in which the light source can be, each light-source mode resulting from the particular combination of light-emitting-element modes, in which each LEE of the light source can be, wherein an LEE can have one of two possible light-emitting-element modes, either an "on mode" or a "down mode" respectively. This can mean that, for different light-source modes, different LEEs and/or a different number of LEEs can be in the on mode and in the down mode respectively. The term "down mode" can be used to indicate a mode, in which less electric current or no current at all flows in the LEE when compared to the "on mode". The term "down mode" may thus refer to both an "off mode (no current)" and a "reduced current mode". A "light-source mode," can therefore be a mode, in which the light source is not completely off. It can be clear, that in addition, a light source might be also switched off completely such that all LEEs are off, as in the case when for example, the optical system is off. However, for the purpose of the present disclosure, "switchable between at least two light-source modes" can mean switchable between at least two light-source modes, wherein in each mode at least one LEE can be in the on mode.

In a "light-source-lifetime-extending mode (LEM)," at least one S-LEE can be in the down mode and, in a "light-source-lifetime-non-extending mode (non-LEM)," all the S-LEEs can be in the on mode but, in all light-source modes, at least one L-LEE can be in the on mode. These light-source modes may thus comprise a non-LEM, in which all LEEs can be in the "on mode" as well as a LEM, in which only one S-LEE can be in the "down mode" mode. According to one embodiment, the light source comprises only one S-LEE. There is therefore one LEM in which this S-LEE is in the down mode and one non-LEM, in which it is in the on mode.

According to some embodiments, the light source can comprise a plurality, i.e. a number n equal or greater than 2, of S-LEEs. According to some LEMs, only one at a time of the S-LEEs or a number of S-LEEs smaller than n can be in the on mode when needed, while the rest can be in the down mode. According to another LEM, all the S-LEEs can be in the down mode when not needed.

According to some embodiments, the light source can comprise a plurality, i.e. a number n equal or greater than 2, of S-LEEs of the same type. "Same type" herein can mean emitting light of the same wavelength or wavelength band and having the same expected lifetime. According to some LEMs, only one at a time of the LEEs or a number smaller than n can be in the on mode when needed, while the rest can be in the down mode. According to another LEM, all the S-LEEs can be in the down mode when not needed.

In combination with any of the above embodiments, the light source may comprise one or more L-LEEs, wherein in each light-source mode at least one of the L-LEEs can be in the on mode. Since extending the expected lifetime of an L-LEE may not contribute to extend the expected lifetime of the light source as extending the expected lifetime of an S-LEE, even when one or more L-LEEs is in the down mode, it can be called non-LEM.

The optical system can comprise a controlling unit for switching the optical system between at least two light-source modes chosen from at least one LEM and at least one non-LEM. This can mean that the light source can be switchable between a LEM and a non-LEM and/or vice versa and/or switchable between a LEM and at least another LEM.

"Switchable" can mean that the light source, in particular at least one LEE of a plurality of LEEs, possibly more than one or all LEEs of the light source can be individually electronically controllable. In the down mode, this can mean interrupting an electric connection or reducing the supply of power to a respective individual LEE. In the on mode, this can mean establishing an electric connection or increasing the supply of power to a respective individual LEE. Thus, switching between light-source modes can mean changing power distribution within the light source such that different LEEs can be electrically powered or differently electrically powered in different light-source modes respectively.

In general, it can be preferred to switch on or leave on as many LEEs as possible, at least as many L-LEEs as possible, preferably all L-LEEs in case of a plurality of L-LEEs, when switching between light source modes. In this way, the heat generated by the LEE or LEEs in the on mode can contribute to maintain a thermal equilibrium of the light-source, such that the temperature of the LEE or LEEs that are in the down mode in a particular light-source mode can remain closer to the temperature of the same LEE or LEEs in a light source mode when they are in the on mode, compared to a mode of the light-source, in which all light emitting elements can be in the down mode. A characteristic of the light source can therefore be that to enable thermic conduction, i.e. heat transfer between LEEs. The LEEs can be mounted on the same substrate or chip board, or otherwise mounted close to each other, in thermal contact. The temperature of the light source can thus remain closer to an average operational temperature between different light-source modes. This can make it possible to reach the operational temperature of a selected light-source mode more quickly and more reliably when switching from a different light-source mode to that selected light-source mode, while increasing the temperature stability, and therefore minimizing changes in emission intensities and spectral shifts.

The "operational temperature" of the light source can be defined as the actual temperature of the light source in a light-source mode. Different light-source modes may have different operational temperatures.

According to some embodiments, the system can comprise a temperature regulator to maintain the light source within a light-source mode temperature range. The light-source mode temperature range may be the same for different light-source modes or different for different light-source modes. The "temperature regulator" can be a device with at least one of the following functions, possibly both, i.e. to take away heat from the light source and/or to provide the light source with heat in a controlled manner. This temperature regulator may be a fluid-based flow-through device transporting heat and/or removing heat from the light source. It may also be a device utilizing a resistive heating in combination with dissipative cooling.

The temperature regulator may comprise a cooling device such as a heat sink or fan to prevent overheating of the light source. The temperature regulator may comprise at least one heating element. According to one embodiment, the at least one heating element can be an LEE with the specific function of heating the light source. According to one embodiment, the at least one heating element can be an LEE with a dedicated function of heating element, for example, an L-LEE, which can be in the down mode, when a S-LEE is in the on mode, and can be in the on mode when an S-LEE is in the down mode. Power may be provided to the LEE heating element with the specific purpose of heating without causing emission of light. According to one embodiment, the at least one heating element can be a resistive element in the light source, for example, in a chip board, on which one or more light LEEs may be mounted. There may be a heating element in correspondence to each LEE. According to one embodiment, the heating element can be controlled such as to provide power used for generating heat to the light source in a LEM that can be equivalent to the power dissipation a non-LEM, wherein the power dissipation can be the difference between the electrical power provided to an LEE minus the power emitted as light, which can be the power dissipated as heat. In this way, an amount of heat can be generated, which can be equivalent to the heat generated by an LEE or LEEs in the on mode, without however that same LEE or LEEs emitting light. This can make possible to achieve an even greater thermal equilibrium, without requiring temperature measurement and accurate temperature control. This can be possible because the lifetime of an LEE can be affected by temperature when the LEE in in the on mode, i.e. when it is emitting light, while the lifetime of an LEE may not be affected or only minimally affected by temperature when it is not emitting light or is in the down mode. The heating element may be however also a thermoelectric element, also called Peltier element, in thermal contact with the light source either directly or via the heat sink. The thermoelectric element may be positioned on the surface of the heat sink or inside the heat sink, for example, between the light source and the heat sink. Depending on the current verse thermoelectric elements can also function as coolers as well as heaters. In this sense, a "heating element" may encompass also the meaning of cooling element, i.e. used at least for heating, but possibly also for cooling. The temperature regulator may comprise at least one temperature sensor by measuring, for example, the ambient temperature and/or the temperature of heat regulator, for example, of a heating element or heat sink and/or the temperature of the light source, for example, the temperature of the socket or chip board of the light emitting elements, and using the measured temperature value or values for a more accurate temperature control of the light source.

According to one embodiment, the heating element can be switchable between a heating element operational mode, in which the heating element can be in the on mode (heating mode) to maintain the light source within a light-source mode temperature range, for a time frame during which the system is in a LEM, and a heating element down mode for a time frame during which the system can be in a non-LEM. With respect to the "down mode", an analogous meaning to that given above with reference to a light-emitting-element mode can also be given. Therefore the heating element down mode may comprise a heating element off mode (no current) as well as a heating element reduced current mode. A "light-source mode temperature range" can be a temperature range comprising the operational temperature typical of a light-source mode. According to one embodiment, the range can be comprised between about 90% of the operational temperature and about 105% of the operational temperature of that light-source mode.

According to some embodiments, the system can comprise a light source comprising a plurality of LEEs, the LEEs may not necessarily have different expected lifetimes, and a controlling unit for switching the system between at least two LEMs. The system can further comprise a temperature regulator to maintain the light source within a light-source mode temperature range, wherein in different LEMs respectively different LEEs or a different number of LEEs can be in the down mode and wherein at least one LEE can be in the on mode. The temperature regulator may be controlled to maintain the light source within the same light-source mode temperature range.

According to some embodiments, the light source can comprise at least one L-LEE emitting white light or light with a wavelength greater than about 450 nm and at least one light emitting element with shorter expected lifetime emitting light with a wavelength equal or smaller than about 450 nm.

The optical system may comprise an optical detector and a cuvette holder for holding one or more optical cuvettes arranged such that light can be guidable in an optical path from the light source through a cuvette held in the cuvette holder to the detector for the photometric measurement of a sample contained in the cuvette. The cuvette holder may be embodied as a frame, comprising, for example, a plurality of cavities or recesses for receiving a respective number of cuvettes. It may be embodied, for example, as a translatable or rotatable array, in which cuvettes may be arranged at regular intervals. It may be for example in the form of a rotor or frame inserted on a rotor rotatable about a symmetry axis.

According to one embodiment, the cuvette holder can be movable in a direction substantially orthogonal to the optical path so that one cuvette at a time can be brought in the optical path for a photometric measurement. The photometric measurement may take place during the movement of the cuvette holder, taking one cuvette at a time in the optical path with a continuous cycle. The optical system may thus be set up to operate at high throughput, wherein a measurement can be taken every few milliseconds.

According to one embodiment, the system can comprise an optical detector and a multi-well-plate holder for holding at least one multi-well-plate arranged such that excitation light can be guidable in an optical path from the light source to at least one well of the multi-well-plate and emission light can be guidable from the at least one well to the detector for the photometric measurement of a sample contained in the well.

The optical path may comprise optical path components which can make it possible to guide light to or through a sample or a plurality of samples in parallel, in a controlled manner, and to measure optical transmission, such as absorption and/or scattering or reflection, or emission light such as fluorescence. The optical system may be however configured to carry out spectroscopic measurements. It may also entail temporally static measurements, time resolved measurements, or both.

The optical path components may be for example lenses, mirrors, apertures, filters, shutters, fiber optics or other waveguide element, a dispersion element, and the like. A dispersion element may be a transmission or reflection diffraction grating, and may be a scanning monochromator or a polychromator, which can be configured to receive transmitted light and disperse it into multiple spectral components. A dispersion element may be also a refractive element, such as a prism.

According to one embodiment, the optical system can comprise a light mixing element comprising light shaping and homogenizing optics, such as for example a mixing rod, for homogenizing the light emitted by the plurality of light emitting elements and improving illumination uniformity before illuminating a sample being located in the optical path. The sample may be located, for example, in a cuvette, flow-through cell, or the like, being located in the optical path.

A "detector" can be an optical detector or photodetector which can be a device that can convert electro-magnetic energy into an electrical signal, including both single element and multi-element or array optical detectors. Thus an optical detector can be a device capable of monitoring an optical electro-magnetic signal and providing an electrical output signal or response signal relative to a baseline signal indicative of the presence and/or concentration of an analyte in a sample located in the optical path. Such devices include, for example, photodiodes, including avalanche photodiodes, phototransistors, photoconductive detectors, linear sensor arrays, CCD detectors, CMOS optical detectors, including CMOS array detectors, photomultipliers, and photomultiplier arrays. According to some embodiments, an optical detector, such as a photodiode or photomultiplier, may contain additional signal conditioning or processing electronics. For example, an optical detector may include at least one pre-amplifier, electronic filter, or integrating circuit. Suitable pre-preamplifiers include integrating, transimpedance, and current gain (current mirror) pre-amplifiers. According to one embodiment, the detector can be of the CCD or CMOS type. According to another embodiment the detector can be of the photodiode or PMT type.

The controlling unit may be embodied as a programmable logic controller running a computer-readable program provided with instructions to perform operations in accordance with a process operation plan. It may be programmed to switch between light-source modes according to the wavelengths needed in a predefined sequence of measurements. According to one embodiment, it can be programmed to switch to a LEM when no measurement is planned in a certain timeframe and to switch to a non-LEM when one or more measurements are planned. According to one embodiment, it can be programmed to switch from a LEM to another LEM according to the wavelength needed at a given time for a given measurement. According to one embodiment, it can be programmed to switch the light-source mode after each measurement or after a series of measurements. According to one embodiment, it can be programmed to switch the light-source mode after a predefined time, during which one or more measurements may take place.

The controlling unit may in particular be set up to control the switching of one or more individual LEEs between the on mode and the down mode respectively and/or the switching of the heat regulator between the heating element operational mode and the heating element down mode in coordination with the number, the type and the throughput of the measurements. For example, it may be synchronized with a predefined cycle time of a series of measurements, for example, with the movement of a cuvette holder in the optical path.

A method for extending the expected lifetime of a light source can comprise a plurality of LEEs with different expected lifetimes mounted on the same substrate or chip board in thermal contact with each other such as to enable thermic conduction and heat transfer between the LEEs. The method can comprise switching between light-source modes chosen from including at least one LEM and at least one non-LEM. In the at least one LEM, the method can comprise switching at least one S-LEE in the down mode. In the at least one non-LEM, the method can comprise switching all the S-LEEs in the on mode. In all light-source modes, the method can comprise switching or leaving at least one L-LEE on. According to one embodiment, the method can comprise maintaining the light source within the same light-source mode temperature range.

A method for extending the expected lifetime of a light source can comprise a plurality of LEEs. The LEEs may not necessarily have different expected lifetimes. This method can comprise switching between at least two LEMs wherein in different LEMs respectively, the method can comprise switching or leaving at least one LEE in the on mode and switching or leaving different LEEs or a different number of LEEs in the down mode. The method can further comprise maintaining the light source within a light-source mode temperature range, which can be the same for different LEMs.

According to some embodiments, in the at least one LEM, the methods can comprise switching to a heating element operational mode and, in the at least one non-LEM, the methods can comprise switching to a heating element down mode wherein in the heating element operational mode, the method can comprise heating the light source.

According to one embodiment, the method can comprise providing power used for generating heat to the light source in a LEM that can be equivalent to the power dissipation in a non-LEM. The methods may comprise switching between light-source modes between two or more photometric measurements respectively.

Figure 1:
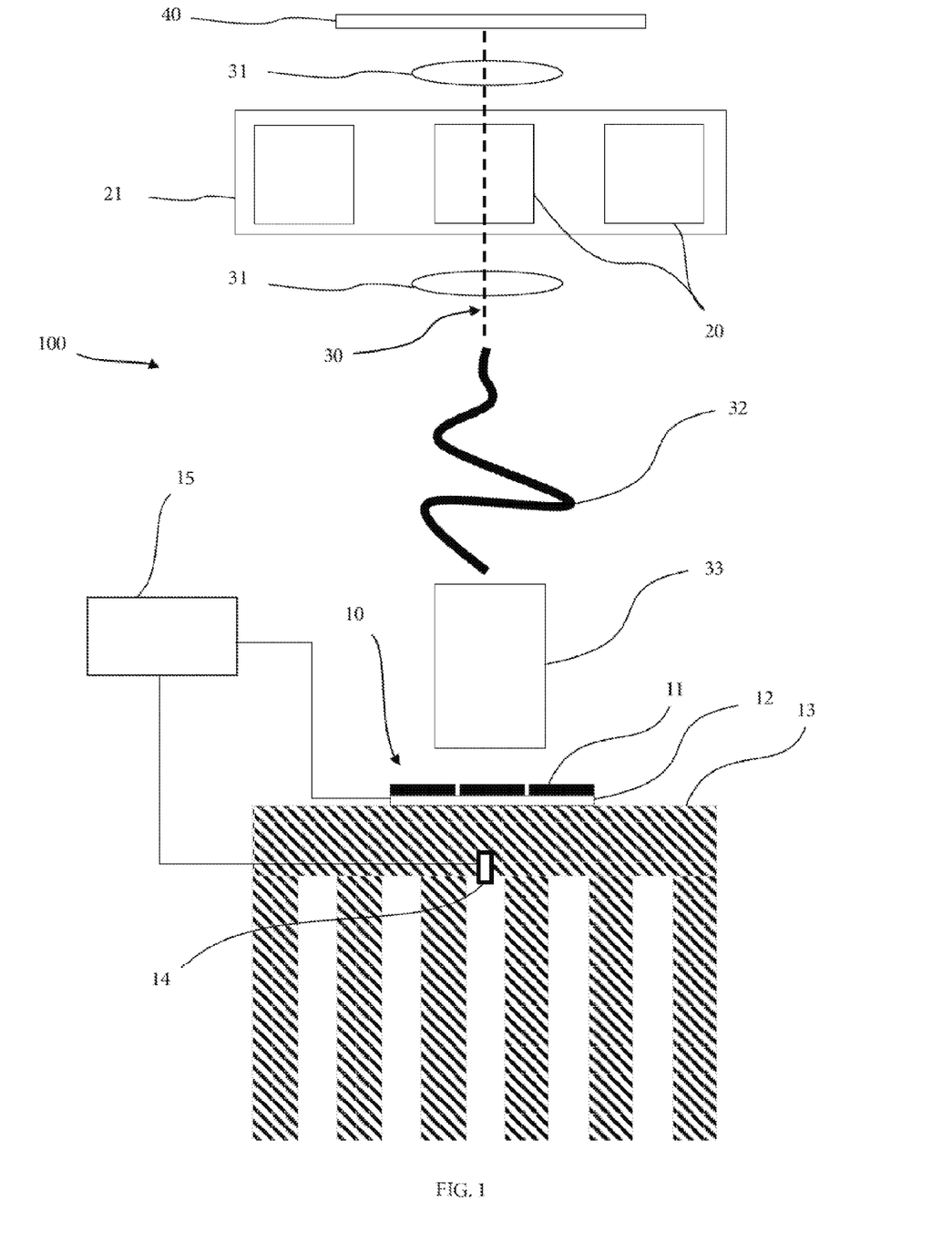
FIG. 1 illustrates schematically an example of optical system for the photometric measurement of samples according to an embodiment of the present disclosure.

Referring initially to FIG. 1, FIG. 1 depicts schematically and not to scale an optical system 100 for the photometric measurement of samples, for example, for determining the presence and/or concentration of analytes in a sample comprised in an optical cuvette 20 held by a cuvette holder 21. The cuvette holder 21 can be a rotor carrying a plurality of cuvettes 20, and transporting one cuvette at a time in the optical path 30 upon rotation. The system 100 can comprise optical path components such as lenses 31, a glass fiber bundle 32, a mixing rod 33, and possibly other components (not shown) such as an aperture, minors, a diffraction grating and the like. The system 100 can further comprise an optical detector 40, comprising an optical sensor such as CCD sensor, which can convert electro-magnetic energy from light coming out of the cuvette 20 located in the optical path 30 into an electrical signal. The sensor 40 may be divided in sectors (not shown), each of which dedicated to a usable wavelength band. The optical system 100 can further comprise a light source 10 comprising a plurality of LEEs 11, for emitting light of respective wavelengths. The light emitting elements 11 can be mounted via a socket on a chip board 12 in thermal contact with each other and with a heat sink 13, made for example of aluminum to dissipate heat from the light source 10. In this example, light from the LEEs 11 can be mixed by the mixing rod 33 and guided through the glass fiber bundle 32 into the optical path 30 though a cuvette 20 to the detector 40 to generate a response signal indicative of the presence and/or concentration of analytes in a sample contained in the cuvette 20.

According to another embodiment, the cuvette holder 21 can be replaced by a multi-well-plate holder (not shown) and the cuvettes 20 can be replaced by a multi-well-plate (not shown). In that case, the optical path components as well as the detector 40 may be arranged differently such that excitation light from the LEEs 11 can be guided to one or more samples located in the wells of the multi-well-plate and emission light can be detected by the detector 40. The optical system 100 can further comprise a controlling unit 15 electrically connected to the chip board 12 for switching the optical system 100 between light-source modes by controlling the switching of one or more individual light emitting elements 11 between the on mode and the down mode respectively.

According to one embodiment, the light emitting elements 11 can have different expected lifetimes and the optical system 100 can be switchable between at least two light-source modes chosen from at least one LEM and at least one non-LEM. In the at least one LEM, at least one LEE 11 with shorter expected lifetime can be in the down mode, in the at least one lifetime-non-extending mode, none of the light emitting elements 11 with shorter expected lifetime can be in the down mode, and in all light-source modes, at least one light emitting element 11 with longer expected lifetime can be in the on mode.

The optical system of FIG. 1 can comprise also a heating element 14 electrically connected to the controlling unit 15. The controlling unit 15 can switch the heating element between a heating element operational mode, for a time frame during which the system 100 can be in a LEM, and a heating element down mode, for a time frame during which the system 100 can be in a non-LEM. The optical system 100 may further comprise at least one temperature sensor (not shown) in thermal contact with the heat sink 13 and/or the chip board 12 electrically connected to the controlling unit 15 such as to measure the temperature and provide temperature data to the control unit.

Figure 2:
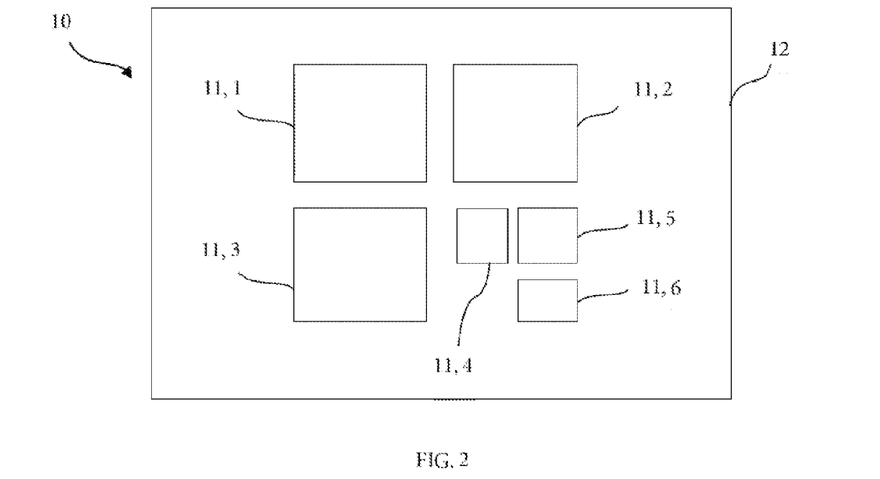
FIG. 2 illustrates schematically an example of light source comprising a plurality of light emitting elements according to an embodiment of the present disclosure.

FIG. 2 shows schematically one possible embodiment of the light source 10 of FIG. 1 in more detail. The light source 10 can comprise six LEDs 11 emitting light of respective wavelengths. The light source 10 can comprise a first LED Chip 11, 1 with longer expected lifetime, for example, about 50,000 hours, emitting light, for example, at about 700 nm. The light source 10 can further comprise a second LED chip 11, 2 with longer expected lifetime, for example, also about 50,000 hours, emitting light in the wavelength band of, for example, about 800-815 nm. The light source 10 can further comprise a third LED chip 11, 3 with longer expected lifetime, for example, also about 50,000 hours, emitting white light. The light source 10 can further comprise a first LED chip 11, 4 with shorter expected lifetime, for example, about 2,000 hours, emitting light of, for example, about 340 nm, which can be a particularly short living LED and the LED with the shortest expected lifetime in this example. The light source 10 can further comprise a second LED chip 11, 5 with shorter expected lifetime, for example, about 10,000 hours emitting light of, for example, about 375 nm. The sixth light emitting element can be a third LED chip 11, 6 with shorter expected lifetime, for example, about 20,000 hours, emitting light in the wavelength band of, for example, about 415-420 nm. All six LED chips 11, 1-6 can be mounted on the same chip board 12 such that thermal equilibrium can be obtained between different LEDs. The LEDs 11, 1-6 can be electrically connected to the controlling unit 15 via the chip board 12 (not shown in FIG. 2).

According to one example, the controlling unit 15 can be set up to switch the light source 10 between two light-source modes according to the sequence and frequency of scheduled photometric measurements. The controlling unit 15 can be set up to switch the light source 10 to a non-LEM when at least one photometric measurement can be scheduled, in which mode all six LEDs 11, 1-6 can be in the on mode. The controlling unit 15 can be further set up to switch the light source 10 to a LEM, wherein only the LEDs with longer expected lifetime 11, 1-3 can be in the on mode and the LEDs 11, 4-6 with shorter expected lifetime can be in the down mode, for a time frame when no photometric measurement is scheduled. Depending on the frequency of the photometric measurements, the switching may occur between two or more measurements.

LEDs 11, 1-3 with longer expected lifetime can be in this example larger than LEDs 11, 4-6 with shorter expected lifetime. LEDs 11, 1-3 can be also in this example higher-power LEDs compared to LEDs 11, 4-6, thereby achieving higher junction temperatures and higher current densities in operation. The contribution of LEDs 11, 1-3 with longer expected lifetime to the temperature of the light source 10 can therefore be larger than the contribution of the LEDs 11, 4-6 with shorter expected lifetime. Thus, in the LEM, the temperature of the light source 10 can remain closer to the operational temperature in the non-LEM than it can be if the entire light source 10 can be switched off. Establishment of the operational temperature in the non-LEM can be thus achieved more quickly when switching from the LEM to the non-LEM. Also, switching can be carried out as frequent as desired. This effect can be better understood with reference to FIG. 3.

Figure 3:
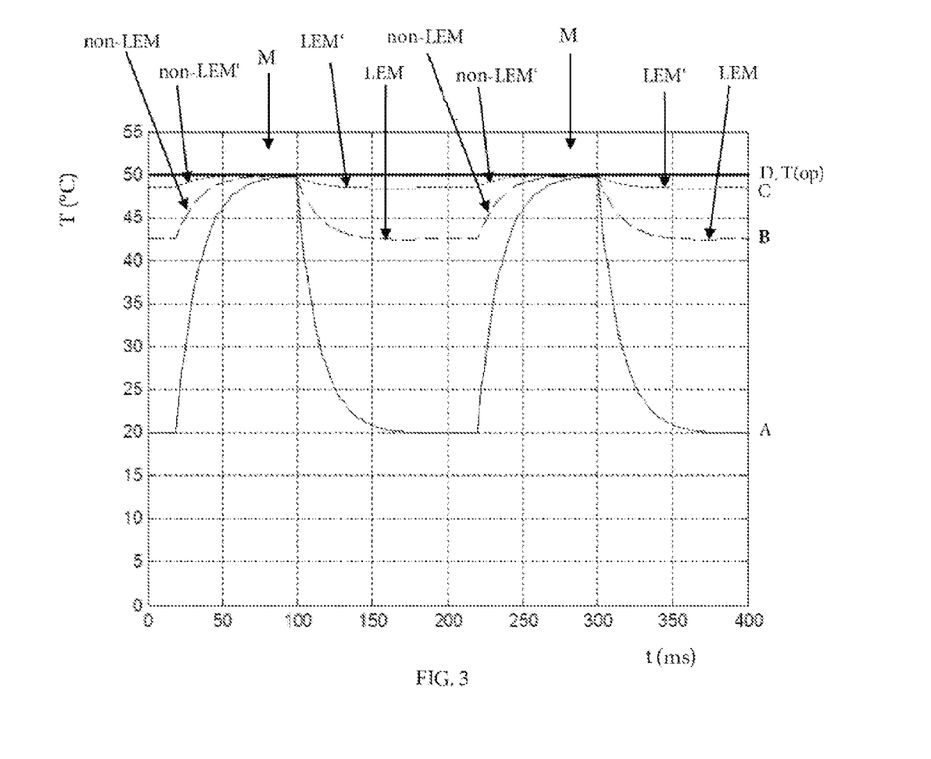
FIG. 3 illustrates a graph showing the temperature control versus time obtained when switching between different light source modes according to an embodiment of the present disclosure.

FIG. 3 is a graph showing an example of how the temperature T in degrees centigrade (° C.) varies versus time t in milliseconds (ms), when switching between different light-source modes, with reference to the optical system of FIG. 2. In a time frame from about 0 to about 400 ms, two photometric measurements M can take place in two time frames of about 80 ms each separated by about 120 ms between consecutive measurements M, wherein 120 ms can be the time that it can take to bring a new cuvette into the optical path 30, in this example. This can be an example of high-throughput optical system where several measurement per second may take place, for example, on the fly while the cuvette holder 21 is moving to bring continuously without stopping one cuvette 20 after another in the optical path 30. Line D is a reference line indicating the operational temperature T(op) achieved by the light source 10 and maintained constant by leaving the light source 10 always on, i.e. with all LEDs 11, 1-6 on, i.e. always in the non-LEM, while cooling down by the heat sink 13, which can dissipate heat to the ambient. Line A is another reference line indicating how the temperature T changes if the light source 10 is switched off completely after each photometric measurement M in order to extend the expected lifetime. In this case, the temperature difference between the operational temperature T(op) and the down temperature T when the light source is completely off can be about 30° C. It can be seen that it can take nearly about 70 ms for the light source 10 to reach the operational temperature T(op) out of about 80 ms available for the measurement M. This can correspond to an average variation of the emission intensity of about 50-60% as well as to an average spectral shift of about 4-8 nm during the first 70 ms of the 80 ms measurement window. Line B shows what happens instead when the system is switched between the non-LEM, in which all LEDs 11, 1-6 are in the on mode, during a measurement M, and the LEM, in which only the LEDs 11, 1-3 with longer expected lifetime are in the on mode and the LEDs 11, 4-6 with shorter expected lifetime are in the down mode, between two consecutive measurements M. In this case, the temperature difference between the operational temperature T(op) in the non-LEM and the down temperature T in the LEM can be only about 7.5° C. It can be seen that it can take a shorter time to reach the operational temperature T(op) when the light source mode is switched from the LEM to the non-LEM. This can correspond to an average variation of the emission intensity of only about 10-15% as well as to an average spectral shift of only about 1-2 nm and for a shorter fraction of the 80 ms measurement window M. While this may be acceptable in order to perform a reliable and high-throughput optical analysis, the expected lifetime of the LEDs 11, 4-6 with shorter expected lifetime can thereby be extended of about 2.5 times by switching to the LEM during the time a new cuvette 20 is brought into the optical path 30. This may not take into account the additional gain in lifetime due to reduced thermal stress in comparison with line A. Thus, by extending the expected lifetime of the LEDs 11, 4-6 with shorter expected lifetime, the expected lifetime of the entire light source 10 can thus be extended, while variations of emission intensity and spectral shifts have been minimized. The expected lifetime of the light source can be extended even more, for example, of 10 times or more depending on how long the timeframe between measurements M or between two series of measurements M is, during which the system is in the LEM. The difference between the operational temperature T(op) in the non-LEM and the down temperature T in the LEM can depend also on how many LEEs remain on in the LEM. In this case, for example, it was sufficient, in order to extend the expected lifetime of the light source 10 of the same amount, to switch in the down mode only the LED 11, 4 with the shortest expected lifetime when switching to the LEM. By leaving therefore 5 LEDs 11, 1,2,3,5,6 on in the LEM, the difference in temperature can thus be minimum and achievement of T(op) when switching to non-LEM even quicker.

Line C shows what happens when the system is switched between a non-LEM', during a measurement M, and a LEM', between two consecutive measurements M. The LEM' is the same as the LEM of line B with the difference that when the system is switched to the LEM', also the heating element 14 is switched to the heating mode. The non-LEM' can be the same as the non-LEM of line B with the difference that when the system is switched to the non-LEM', the heating element 14 can be switched to the down mode. The controlling unit 15 can thus control the switching of both the light source 10 and the heating element 14 in order to reduce even further the temperature difference when switching between-light source modes. By providing power used for generating heat to the light source that can be equivalent to the power dissipation in the non-LEM, the temperature difference can in principle be eliminated (Line D).

Figure 4A:
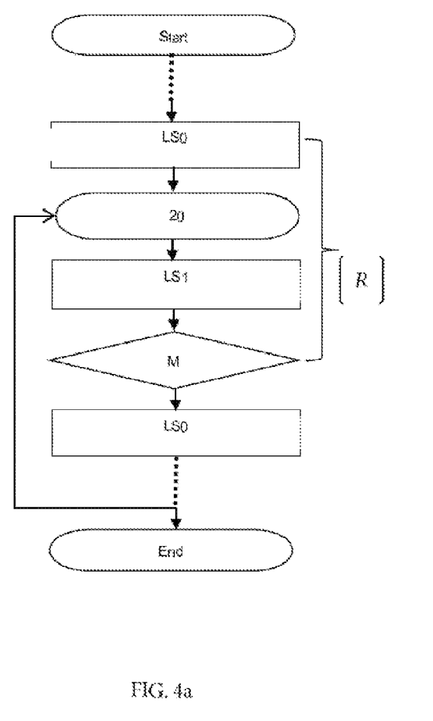
FIG. 4a illustrates a flow diagram of an exemplary method for extending the expected lifetime of a light source according to an embodiment of the present disclosure.

FIG. 4a is a flow diagram of an exemplary method for extending the expected lifetime of a light source 10 such as that of FIG. 1. At start, it can be assumed that the optical system 100 can be off or in stand-by, with the light source off, because for example, used for the first time, or because of maintenance, or because not used for a prolonged time. The light source 10 can thus be switched on once at the beginning, for example, just before a measurement M has to take place. The light source 10 can thus be switched to one of the possible LEMs (LSO), in which at least one L-LEE 11, 1-3 can be switched in the on mode and at least one S-LEE 11, 4-6 can be switched in the down mode, for example, a mode in which all L-LEEs 11, 1-3 can be in the on mode and all S-LEEs 11, 4-6 can be in the down mode.

A cuvette 20 containing a sample can then be brought into the optical path 30. The optical system 100 can then be switched to another of more possible light-source modes LS1, which may be a non-LEM or a different LEM, in which the LEE or LEEs 11 emitting light in a wavelength band for the photometric measurement of the sample contained in the cuvette 20 can be switched on, for a time window during which the measurement M can take place. For example, all LEEs 11, 1-6 can be switched in the on mode so that all wavelengths of the light source 10 may be used for the measurement M.

After the measurement M has taken place, the system 100 can be switched back to the same or different LEM LSO, in which, at least one light emitting element 11 can be in the down mode, and at least one LEE 11 can remain on, for example, the same mode, in which all L-LEEs 11, 1-3 can be in the on mode and all S-LEEs 11, 4-6 can be in the down mode.

The system 100 can remain in this LEM LSO until a new cuvette 20 is brought into the optical path 30 and the process can begin over again. It may thus be repeated a number R of times, wherein the system can be switched between light-source modes between two consecutive measurements M.

In a LEM LS0, the method may optionally comprise a heating step, in which the heating element 14 can be in the heating mode. In a light source mode LS1, the method may comprise switching the heating element 14 in the down mode.

The method can end after a series of samples have been analyzed, i.e. after a series of measurements M has taken place. The optical system 100 can thus remain in the LEM LSO until a new series of measurements M starts or the optical system 100 is switched off.

Figure 4B:
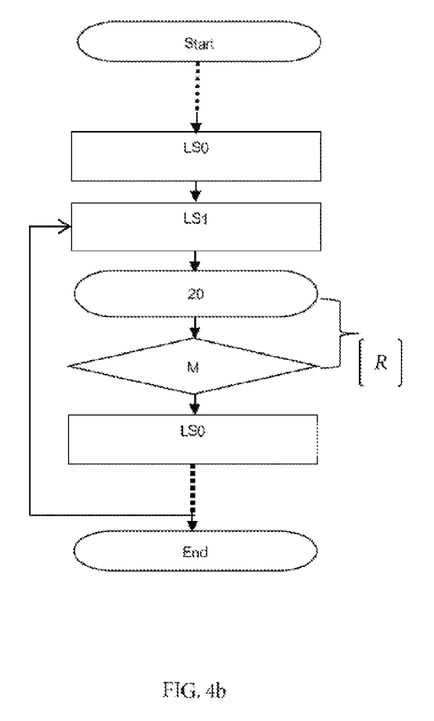
FIG. 4b illustrates a flow diagram of an exemplary method for extending the expected lifetime of a light source according to another embodiment of the present disclosure.

FIG. 4b is a flow diagram of another exemplary method for extending the expected lifetime of a light source 10 such as that of FIG. 1. The method of FIG. 4b is basically the same of the method of FIG. 4a with the following difference. The optical system 100 can be switched from a light-source mode LS0, for example, from a LEM LSO to a light-source mode LS1 when a series of measurements M starts. The light-source mode LSO being one LEM, in which at least one L-LEE 11, 1-3 can be switched in the on mode and at least one S-LEE 11, 4-6 can be switched in the down mode, for example, a mode in which all L-LEEs 11, 1-3 can be in the on mode and all elements-LEEs 11, 4-6 can be in the down mode. The light-source mode LS1 being a non-LEM or a different LEM, in which the LEE or LEEs 11 emitting light in a wavelength band for the photometric measurements of the samples in the series can be switched in the on mode, for example, all LEEs 11, 1-6 can be switched in the on mode. The optical system 100 can then be switched back from the light-source mode LS1 to the LEM LSO when the series of measurements M is over, rather than between every two consecutive measurements M. The optical system 100 can thus remain in the LEM LS0 until a new series of measurements M can start or the optical system 100 can be switched off.

According to some embodiments, the light source 10 may comprise any combination of LEEs 11, regardless of their relative expected lifetime. The methods of FIG. 4a and FIG. 4b may then comprise the respective steps of switching between at least two LEMs LS0, LS1, wherein in different LEMs, LS0, LS1 respectively, the method can comprise switching or leaving at least one LEE 11 in the on mode and switching or leaving different LEEs 11 or a different number of LEEs 11 in the down mode. The method can further comprise maintaining the light source 10 within the same light-source mode temperature range when switching between LEMs LS0, LS1. This may be achieved by switching the heating element into the appropriate heating element mode when switching the LEMs LS0, LS1.

In summary, a system can be comprised of a light source comprising a plurality of light emitting elements and a controlling unit for switching between light source modes in which different light emitting elements or a different number of light emitting elements can be switched between an on mode and a down mode respectively. In all light source modes, one or more light emitting elements, such as, those with longer expected lifetime, can remain in the on mode, while one or more light emitting elements, such as, those with shorter expected lifetime, may be switched in the down mode.

In this way, a thermal equilibrium of the light source can be maintained by the heating of the light emitting element or elements which can remain in the on mode, i.e. a stable operational temperature can be obtained more quickly and more reliably when switching between light source modes, due to retention of heat in the light source itself.

By providing power to the light source in an amount equivalent to the power removed from a light emitting element or elements in the down mode, such as to generate an amount of heat equivalent to the heat generated by the same light emitting element or elements by power dissipation in the on mode, an even greater thermal equilibrium can be achieved, without requiring temperature measurement and accurate temperature control.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An optical system for the photometric measurement of samples, the optic system comprising:
a light source, the light source comprising a plurality of light emitting elements (LEEs) mounted on the same substrate or chip board in thermal contact with each other such as to enable thermic conduction and heat transfer between the LEEs, the LEEs having different expected lifetimes; and
a controlling unit for switching the optical system between at least two light-source modes chosen from at least one light-source-lifetime-extending mode (LEM) and at least one light-source-lifetime-non-extending mode (non-LEM), wherein in the at least one LEM, at least one light emitting element with shorter expected lifetime (S-LEE) is in a down mode and in the at least one non-LEM, all S-LEEs are in an on mode and wherein in the at least one LEM and in the at least one non-LEM, at least one light emitting element with longer expected lifetime (L-LEE) is in the on mode.

2. The optic system according to claim 1, wherein the light source comprises a plurality of S-LEEs of the same type.

3. The optic system according to claim 1, wherein the optical system is switchable between a non-LEM, wherein all LEEs are in the on mode, and a LEM or between two or more LEMs wherein in different LEMs respectively different S-LEEs or a different number of S-LEEs are in the down mode.

4. The optic system according to claim 1, further comprising,
a temperature regulator to maintain the light source within a light-source mode temperature range.

5. An optical system for the photometric measurement of samples, the optic system comprising:
a light source, the light source comprising a plurality of light emitting elements (LEEs) mounted on the same substrate or chip board in thermal contact with each other such as to enable thermic conduction and heat transfer between the LEEs;

a controlling unit for switching the optical system between at least two light-source-lifetime-extending modes (LEMs); and a temperature regulator to maintain the light source within a light-source mode temperature range, wherein in different LEMs respectively different LEEs or a different number of LEEs are in the down mode and wherein at least one LEE is in the on mode.

6. The optic system according to claim 5, wherein the temperature regulator comprises at least one heating element in thermal contact with the light source and wherein the heating element is switchable between a heating element operational mode for a time frame during which the optic system is in a LEM and a heating element down mode for a time frame during which the system is in a non-LEM.

7. The optic system according to claim 5, wherein the light source comprises at least one L-LEE emitting white light or light with a wavelength greater than 450 nm and at least one S-LEE emitting light with a wavelength equal or smaller than 450 nm.

8. The optic system according to claim 5, further comprising, an optical detector; and a cuvette holder for holding one or more optical cuvettes arranged such that light is guidable in an optical path from the light source through a cuvette held in the cuvette holder to the optical detector for the photometric measurement of a sample contained in the cuvette.

9. The optical system according to claim 8, wherein the cuvette holder is movable in a direction orthogonal to the optical path so that one cuvette at a time can be brought in the optical path for a photometric measurement.

10. The optical system according to claim 5, further comprises, an optical detector; and a multi-well-plate holder for holding at least one multi-well-plate arranged such that excitation light is guidable in an optical path from the light source to at least one well of the multi-well-plate and emission light is guidable from the at least one well to the optical detector for the photometric measurement of a sample contained in the well.

11. A method for extending the expected lifetime of a light source comprising a plurality of light emitting elements LEEs mounted on the same substrate or chip board in thermal contact with each other such as to enable thermic conduction and heat transfer between the LEEs, the LEEs having different expected lifetimes, the method comprising:

switching between light-source modes chosen from at least one light-source-lifetime-extending mode (LEM) and at least one light-source-lifetime-non-extending mode (non-LEM);

switching at least one light emitting element with shorter expected lifetime (S-LEE) in a down mode when in the at least one LEM;

switching all the S-LEEs in an on mode when in the at least one non-LEM; and switching or leaving at least one light emitting element with longer expected lifetime (L-LEE) in the on mode when in all light-source modes.

12. A method for extending the lifetime of a light source comprising a plurality of light emitting elements (LEEs), the method comprising:

switching between at least two light-source-lifetime-extending modes (LEMs) wherein in different LEMs respectively;

switching or leaving at least one LEE in an on mode and switching or leaving different LEEs or a different number of LEEs in an down mode; and maintaining the light source within the same light-source mode temperature range when switching between light-source modes.

13. The method according to claim 12, further comprises, switching to a heating element operational mode when in the at least one LEM;

switching to a heating element down mode when in the at least one non-LEM; and heating the light source when in the heating element operational mode.

14. The method according to claim 13, further comprises, providing power used for generating heat to the light source that is equivalent to the power dissipation in the at least one non-LEM when in the heating element operational mode.

15. The method according to claim 12, further comprises, switching between light-source modes between two or more photometric measurements respectively.

\* \* \* \* \*